United States Patent [19]

Kimura et al.

[11] 4,273,673
[45] Jun. 16, 1981

[54] RUST INHIBITORS AND COMPOSITIONS OF SAME

[75] Inventors: Shoji Kimura, Heiwa; Noboru Ishida, Kanagawa, both of Japan

[73] Assignee: Nippon Oil Company Ltd., Tokyo, Japan

[21] Appl. No.: 68,901

[22] Filed: Aug. 23, 1979

Related U.S. Application Data

[62] Division of Ser. No. 958,632, Nov. 8, 1978, abandoned.

[30] Foreign Application Priority Data

Nov. 30, 1977 [JP] Japan .................................. 52-142602

[51] Int. Cl.³ ............................................. C23F 11/12
[52] U.S. Cl. ................................ 252/396; 106/14.22; 106/14.26; 422/12; 568/648
[58] Field of Search ................... 252/396; 106/14.22, 106/14.26; 422/12; 568/648

[56] References Cited

U.S. PATENT DOCUMENTS

| | | | |
|---|---|---|---|
| 2,075,018 | 3/1937 | Bruson et al. | 568/648 |
| 2,166,518 | 7/1939 | Caplan | 568/648 |
| 2,434,797 | 1/1948 | Harvey | 568/648 |
| 2,486,925 | 11/1949 | Carroll | 568/648 |

FOREIGN PATENT DOCUMENTS 368926 6/1961 Japan .

*Primary Examiner*—Deborah L. Kyle
*Assistant Examiner*—Irwin Gluck

[57] ABSTRACT

There is disclosed a rust inhibitor comprising glycerol-1-alkylphenoxy-3-glycerol ether of the formula

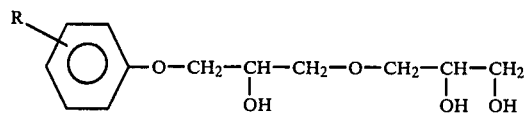

wherein R is an alkyl group of $C_{6-18}$.

A composition having rust preventing effect may be obtained by adding the rust inhibitor to a mineral oil.

4 Claims, No Drawings

RUST INHIBITORS AND COMPOSITIONS OF SAME

This is a division of application Ser. No. 958,632 filed Nov. 8, 1978, now abandoned.

BACKGROUND OF THE INVENTION

Hitherto, there can be found two kinds of uses in a rust inhibitor, one is use of same to provide rust preventing effect to a lubricant such as turbine oil, engine oil, gear oil or hydraulic fluid and the other is use of same as an ingredient in so-called rust preventive oils which prevent rusting of a metallic product.

Primary properties required in these inhibitors are to have enough solubility to a mineral oil used and to adsorb to a metal surface strongly to prevent water, salts, corrosive gases (NOx, SOx) and dust from attacking chemically on metal surface which cause rusting.

In the past, organocarboxylic acids, salts or esters thereof, sulfonates, amines, phosphoric acid and salts or esters thereof have been well-known as a rust inhibitor. As an industrial lubricant organocarboxylic acids, especially alkenyl succinic acid and esters thereof have been primarily used. And as a rust preventive oil organocarboxylic acid esters have typically been used.

The alkenyl succinic acid and its derivatives have been apt to interfere with the operation of machines due to the fact that corrosion could occur to effect precipitates and/or adhesive substances by their strong acidic carboxyl groups when they are brought into contact with non-ferrous metals, for example, copper-tin alloy, copper-zinc alloy and the like.

The organocarboxylic acid esters have a similar drawback by the fact that their ester bonds used to be cleaved by their hydrolysis due to moisture and heat derived from their environment to isolate carboxyl groups.

Further, these rust inhibitors often form precipitates and/or sludges by a chemical reaction when they are brought into contact with basic substances thereby becoming the origin of a trouble in case of being used jointly with basic additives or in the case of being used in ammonia compressor lubricants.

On the other hand, the organocarboxylic acid esters also form an acid by the hydrolysis of their ester bonds as mentioned above and the acid causes discoloring of a metal surface.

In addition to the above noted, they have lower demulsibility.

Inventors of the present invention arrived at the present invention as a result of serious efforts for developing a rust inhibitor not having the aforementioned drawbacks. In order to avoid the above drawbacks, three chemically neutral hydroxy groups, selected as polar groups, are combined with an oleophilic group of the rust inhibitor through an ether bond.

SUMMARY OF THE INVENTION

An object of the present invention, therefore, is to provide a rust inhibitor not having the drawbacks usually encountered in conventional rust inhibitors, which comprises glycerol-1-alkylphenoxy-3-glycerol ether of the formula

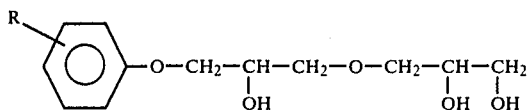

wherein R is an alkyl group of $C_{6-18}$.

Another object of the present invention is to provide a composition having superior rust preventing ability.

A further object of the invention is to provide a composition obtained by adding the above rust inhibitor to a mineral oil.

DETAILED DESCRIPTION OF THE INVENTION

Glycerol-1-alkylphenoxy-3-glycerol ether according to the present invention may be prepared by, for example, heating alkylphenylglycidyl ether and glycerin in the presence of metallic sodium catalyst.

The number of carbon atoms of the alkyl group substituted for the phenyl group of the above ether is 6-18. The alkyl group is preferably in the sequence of nonyl, dodecyl, pentadecyl, hexyl and octadecyl, and the most preferable alkyl group is nonyl group of $C_9$.

In the case where the carbon number of the alkyl group is less than 6, solubility of the glycerol ether obtained to a mineral oil is so poor that the resulting composition has no practical use. On the contrary, glycerol-alkylphenoxy-3-glycerol ether having an alkyl group of more than 18 carbon atoms has better solubility but is poor in rust inhibitability.

The carbon number used heretofore refers to the carbon number of a primary ingredient in the ether and a small amount of alkyl groups having a slightly different carbon number may be present.

The alkyl group may be located at any position, for example, at o, m or p-position of the benzene nucleus, but it is preferable that the alkyl group is located at the p-position.

The mineral oil referred to in the present specification is the one generally used as a base oil of a lubricant or a rust preventive oil, for example, lubricant fraction of naphthenic or paraffin oils having 20-150 cSt. of viscosity at 37.8° C., refined products thereof, petroleum solvents, petrolatum and the like.

The aforesaid glycerol-1-alkylphenoxy-3-glycerol ether is added to a mineral oil to make lubricants or rust preventive oils.

The amount of the rust inhibitor to be added to a mineral oil is in the range of 0.01–20 wt. parts based on 100 wt. parts of the mineral oil.

In the case where the amount of a rust inhibitor used is less than 0.01 wt. parts per 100 wt. parts of a mineral oil, resulting rust preventing effect is poor and in the case of using more than 20 wt. parts of the rust inhibitor per 100 wt. parts of a mineral oil, sufficient rust preventing effect corresponding to the amount used may not be obtained and such use is commercially unsuitable.

The addition amount of the rust inhibitor for preparing a lubricant is in the range of 0.01–1.0 wt. parts based on 100 wt. parts of a mineral oil used, preferably 0.03–0.5 wt. parts. And the one for preparing a rust preventive oil is in the range of 0.1–20 wt. parts per 100 wt. parts of the mineral oil, preferably 0.5–5 wt. parts.

It is also possible to use other additives jointly with the aforesaid ether in the case of producing a lubricant or a rust preventive oil. In such a case, both acidic and basic materials may be incorporated as additives.

The following is an example for preparing the rust inhibitor according to the present invention.

PREPARATION EXAMPLE

Into a flask, were put 27.6 g (0.1 mol) of p-nonylphenylglycidyl ether and 46.1 g (0.5 mol) of glycerin and the mixture was gradually heated in the presence of 1.15 g (0.05 mol) of metallic sodium to react them for 5 hours at 180° C. under nitrogen atmosphere. Then, the reactants were cooled.

Following the extraction of the resulting product with 500 ml. of ethyl ether, the extract was washed with water and then, ethyl ether was removed, giving 24.1 g of transparent, colorless and viscous glycerol-1-p-nonylphenoxy-3-glycerol ether in liquid form.

In the same manner as described above, glycerol-1-alkylphenoxy-3-glycerol ether of $C_{12}$, $C_{15}$, $C_{16}$ and $C_{18}$ were obtained.

The resulting ethers were evaluated by the following performance tests on the basis of the Japanese Industrial Standard as shown below.

JIS K 2510; Test method for rust-preventing characteristics of turbine oils.

Into a mixture of a sample and water, a test piece of iron is immersed and the mixture is stirred at 60° C. for 24 hours. Thereafter, the presence or absence of rusting on the surface of the test piece is investigated.

JIS K 2517; Testing method for steam emulsion number of lubricating oils.

Steam is blown into a sample until the total volume of the sample and condensed water becomes 52-55 ml and then, the separated state of the sample and condensed water is observed. The demulsibility is determined as number of seconds required by the time where the separation amount of the oil phase becomes 20 ml. It is regarded as "above 1200 seconds" if the amount of the separated oil does not reach 20 ml. after 20 minutes.

JIS K 2515; Testing method for oxidation characteristics of turbine oils.

Oxygen is blown into a sample at 95° C. in the presence of steel wire, copper wire and water to observe surface changes of the metals and the state of water and oil phase.

JIS Z 0236; Testing method for rust preventive oils.

A test piece of steel, coated with a sample, is hung in a humidity cabinet and rotated for 200 hours at 49±1° C. in above 95% relative humidity.

Thereafter, the degree of rusting on the test piece is measured to evaluate same with "A(superior)-E(inferior)."

JIS K 2520; Testing method for emulsion characteristics of lubricating oils.

40 ml of sample is mixed with 40 ml of water at 54±1° C. with stirring to observe the state, separated into water and oil phases, of the resulting emulsion.

The evaluation of the state is shown as:

oil phase (ml)-water phase (ml)-emulsion phase (ml) [time passed (min.)]

The present invention will be further illustrated in more detail by way of the following examples and controls.

EXAMPLES 1-5 AND CONTROL 1

The lubricants used in examples 1-5 were prepared by respectively adding glycerol-1-p-nonylphenoxy-3-glycerol ether, glycerol-1-p-dodecylphenoxy-3-glycerol ether, glycerol-1-p-pentadecylphenoxy-3-glycerol ether, glycerol-1-p-hexylphenoxy-3-glycerol ether and glycerol-1-p-octadecylphenoxy-3-glycerol ether made according to the manner as described in the foregoing Preparation Example to a purified lubricant fraction, obtained from the Minas crude oil, having the viscosity of 56 cSt. at 37.8° C. and the lubricant used in Control 1 was prepared by adding commercially available 2-oxypropyl-2'-alkenylmonosuccinate of the formula

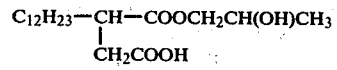

as a rust inhibitor to the above lubricant fraction.

The results of the test for steam emulsion number of lubricating oils and the test for rust preventing characteristics of turbine oils carried out with the above lubricants are shown in Table 1.

TABLE 1

|  | Lubricant composition (parts by wt.) | | Test result | |
|---|---|---|---|---|
|  | Mineral oil | Rust inhibitor | Test for rust preventing characteristics of turbine oils | Test for steam emulsion number of lubricating oils |
| Example 1 | lubricant fraction obtained from Minas crude oil (100) | glycerol-1-p-nonylphenoxy-3-glycerol ether (0.10) | pass | 53 |
| 2 | same as above | glycerol-1-p-dodecylphenoxy-3-glycerol ether (0.10) | " | 74 |
| 3 | same as above (100) | glycerol-1-p-pentadecylphenoxy-3-glycerol ether (0.10) | " | 103 |
| 4 | same as above (100) | glycerol-1-p-hexylphenoxy-3-glycerol ether (0.10) | " | 140 |
| 5 | same as above (100) | glycerol-1-p-octadecylphenoxy-3-glycerol ether (0.10) | " | 220 |
| Control 1 | same as above (100) | alkenyl monosuccinate (0.10) | " | >1200 |

The compositions used in examples 1-5 had excellent performance in each test. On the contrary, the compositions used in control 1 stood the turbine oil anticorrosive test but showed unfavorable result in the test for steam emulsion number of lubricating oils.

It seems that the unfavorable result is due to the hydrolysis of the ester bonds contained in the alkenyl succinic acid ester.

EXAMPLES 6–10 AND CONTROL 2

The lubricants used in examples 6–10 and in control 2 were prepared in the same manner as described in examples 1–5 and control 1.

Using these lubricants, test for oxidation characteristics of turbine oil was carried out. The results obtained are shown in Table 2.

EXAMPLES 11–15 AND CONTROL 3

In Examples 11–15 and Control 3, rust preventive oil made with glycerol-1-p-nonylphenoxy-3-glycerol ether, glycerol-1-p-dodecylphenoxy-3-glycerol ether, glycerol-1-p-octadecylphenoxy-3-glycerol ether, glycerol-1-p-pentadecylphenoxy-3-glycerol ether and glycerol-1-p-hexylphenoxy-3-glycerol ether and with commercially available sorbitan mono-oleate were used to carry out the test for rust preventive oils and the test for emulsion characteristics of lubricating oils. The results

TABLE 2

| Lubricant composition (parts by wt.) | | | Test for oxidation characteristics of turbine oils | | | |
|---|---|---|---|---|---|---|
| Mineral oil | Rust inhibitor | Other additive | oil phase | water phase | iron surface | copper surface |
| Lubricant fraction obtained from Minas crude oil (100) | glycerol-1-p-nonylphenoxy-3-glycerol ether (0.10) | 2.6-ditert.Bu -p-cresol (0.60) | transparent | transparent | lustrous | lustrous |
| same as above | glycerol-1-p-dodecylphenoxy-3-glycerol ether (0.10) | same as above | same as above | same as above | same as above | same as above |
| same as above | glycerol-1-p-pentadecylphenoxy-3-glycerol ether (0.10) | same as above | same as above | same as above | same as above | same as above |
| same as above | glycerol-1-p-hexylphenoxy-3-glycerol ether (0.10) | same as above | same as above | same as above | same as above | same as above |
| same as above | glycerol-1-p-octadecylphenoxy-3-glycerol ether (0.10) | same as above | same as above | same as above | same as above | same as above |
| same as above | alkenyl monosuccinate (0.10) | same as above | rather whity turbid | rather whity turbid | grayish | darkened |

As will be seen from the above Table 2, there was obtained are shown in Table 3.

TABLE 3

| Rust preventing oil composition (parts by wt.) | | Test for rust preventive oils | Test for emulsion characteristics of lubricating oils |
|---|---|---|---|
| Mineral oil | Rust inhibitor | | |
| Purified spindle oil obtained from Arabian crude oil (100) | Glycerol-1-p-nonylphenoxy-3-glycerol ether (0.50) | A | 40-40-0 (5) |
| same as above | glycerol-1-p-dodecylphenoxy-3-glycerol ether (0.50) | A | 40-40-0 (6) |
| same as above | glycerol-1-p-pentadecylphenoxy-3-glycerol ether (0.50) | A | 40-40-0 (7) |
| same as above | glycerol-1-p-hexylphenoxy-3-glycerol ether (0.50) | A | 40-40-0 (9) |
| same as above | glycerol-1-p-octadecylphenoxy-3-glycerol ether (0.50) | A | 40-40-0 (9) |
| same as above | sorbitan monoleate (0.50) | A | 41-38-1 (10) | found no deterioration of oil in the compositions according to the present invention and surfaces of metal pieces used as a catalyst were also clean.

On the contrary, the composition used in control 2 had whity turbid water phase and oil phase.

This seems to have been derived from the hydrolysis of the rust inhibitor used in Control 2. Further, in case of the Control 2, the surfaces of the metals used were lusterless. This will be due to a chemical reaction of the rust inhibitor used in control 2 with the surfaces of the metals used.

As will be seen from the above Table 3, with the compositions according to the present invention, there can scarcely be found an emulsified layer and they are excellent in demulsibility as compared with that of a conventional rust preventive oil and shows excellent performance as a rust preventive oil.

What we claim is:

1. A composition having rust preventing ability which comprises (A) a glycerol-1-alkylphenoxy-3-glycerol ether of the formula

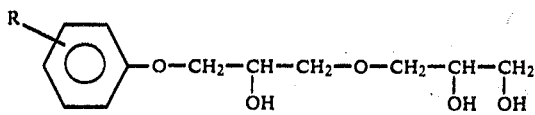

wherein R is an alkyl radical with 9, 12 or 15 carbon atoms and (B) a mineral oil in a weight ratio of 0.01–20 parts of (A) per 100 parts of (B).

2. A composition according to claim 1 wherein said glycerol-1-alkylphenoxy-3-glycerol ether is selected from the group consisting of glycerol-1-p-nonylphenoxy-3-glycerol ether, glycerol-1-p-dodecylphenoxy-3-glycerol ether and glycerol-1-p-pentadecylphenoxy-3-glycerol ether.

3. A method of inhibiting rust formation on metallic surfaces, which comprises admixing (A) glycerol-1-alkylphenoxy-3-glycerol ether of the formula

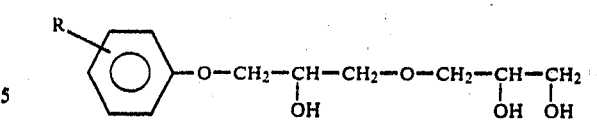

wherein R is an alkyl radical with 9, 12 or 15 carbon atoms, with (B) a mineral oil, in a weight ratio of 0.01–20 parts of (A) per 100 parts of (B); and applying the resulting admixture to a metal surface, whereby rusting is inhibited.

4. The method according to claim 3, wherein said glycerol-1-alkylphenoxy-3-glycerol ether is selected from the group consisting of glycerol-1-p-nonylphenoxy-3-glycerol ether, glycerol-1-p-dodecylphenoxy-3-glycerol ether and glycerol-1-p-pentadecylphenoxy-3-glycerol ether.

* * * * *